United States Patent [19]

Eicken et al.

[11] Patent Number: 5,438,070
[45] Date of Patent: Aug. 1, 1995

[54] CARBOXANILIDES, THEIR PREPARATION AND COMPOSITIONS CONTAINING THEM FOR CONTROLLING HARMFUL FUNGI

[75] Inventors: Karl Eicken, Wachenheim; Hartmann Koenig, Limburgerhof; Eberhard Ammermann, Heppenheim; Gisela Lorenz, Neustadt, all of Germany

[73] Assignee: BASF Aktiengesellschaft, Ludwigshafen, Germany

[21] Appl. No.: 121,549

[22] Filed: Sep. 16, 1993

[30] Foreign Application Priority Data

Sep. 21, 1992 [DE] Germany ............... 42 31 517.4

[51] Int. Cl.⁶ ................. C07D 231/14; A01N 43/56
[52] U.S. Cl. ..................... 514/403; 548/194; 548/364.7
[58] Field of Search ............... 548/369.7; 514/403

[56] References Cited

U.S. PATENT DOCUMENTS 3,505,055  4/1970  Vonschmeling ............ 71/90
4,134,987  1/1979  Huppatz .
5,223,526  6/1993  McLoughlin ............ 514/406

FOREIGN PATENT DOCUMENTS 371950   6/1990  European Pat. Off. .
545099   6/1993  European Pat. Off. .
WO9311117 10/1943 WIPO .
91/01311  2/1991  WIPO .

OTHER PUBLICATIONS

*Chem. Abst.*, vol. 94, No. 15, Apr. 13 1981.
*Acta Phytophathalogica Academiai Scientiarum Hungaricae*, vol. 8 (3–4)1, pp. 269–282 (1973).
Thiphene Carboxamide Fungicides . . . , Pesticide Biochemistry and Physiology 15, 188–204 (1986) White et al.

*Primary Examiner*—Robert Gerstl
*Attorney, Agent, or Firm*—Keil & Weinkauf

[57] ABSTRACT

Carboxanilides of the formula I

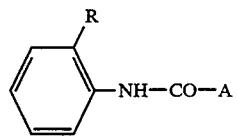

where the substituents have the following meanings:
R is substituted or unsubstituted alkyl, alkoxy, alkenyl, alkenyloxy, alkynyl, alkynyloxy, cycloalkyl, cycloalkenyl, cycloalkyloxy, cycloalkenyloxy or phenyl;
A is one of the radicals A1 to A5

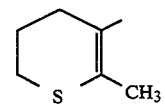

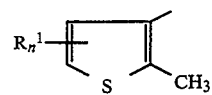

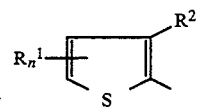

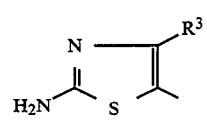

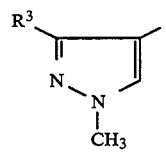

where
$R^1$ is hydrogen or alkyl;
$R^2$ is halogen or alkyl;
$R^3$ is alkyl or haloalkyl;
n is 1 or 2, methods of manufacturing them, and agents containing them and their use for controlling harmful fungi.

6 Claims, No Drawings

CARBOXANILIDES, THEIR PREPARATION AND COMPOSITIONS CONTAINING THEM FOR CONTROLLING HARMFUL FUNGI

The present invention relates to carboxanilides of the formula I

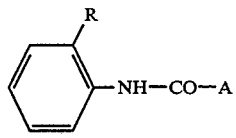

where the substituents have the following meanings:

R
is $C_3-C_{12}$-alkyl, $C_2-C_{12}$-alkoxy, $C_3-C_{12}$-alkenyl, $C_3-C_{12}$-alkenyloxy, $C_3-C_6$-alkynyl, $C_3-C_6$-alkynyloxy, where these groups can be partially or completely halogenated;
$C_3-C_7$-cycloalkyl, $C_4-C_7$-cycloalkenyl, $C_3-C_7$-cycloalkyloxy or $C_4-C_7$-cycloalkenyloxy, where these rings can carry one to three $C_1-C_4$-alkyls;
phenyl, which can carry one to five halogens and-/or one to three of the following radicals: $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio;

A is a cyclic radical from the group consisting of the formulae A1 to A5:

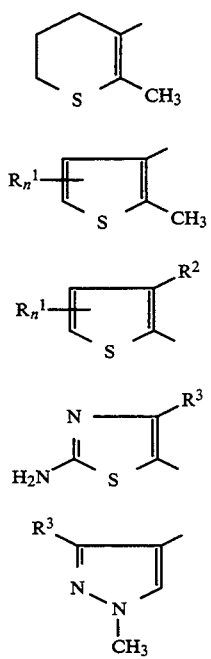

where the substituents have the following meanings:
$R^1$ is hydrogen or $C_1-C_4$-alkyl;
$R^2$ is halogen or $C_1-C_4$-alkyl;
$R^3$ is $C_1-C_4$-alkyl or $C_1-C_4$-haloalkyl;
n is 1 or 2, where the radicals $R^1$ can be different if the value of n is 2,
where R is not phenyl if A is 3-methylthien-2-yl, excluding compounds I where A is A5 and
$R^3$ is methyl if R is cyclopentyl, cyclohexyl or cycloheptyl or where $R^3$ is difluoromethyl if R is cyclohexyl, 4-t-butylcyclohexyl, cyclohexyloxy, cyclohex-1-en-1-yl, 2,6-dimethylcyclohex-1-en-1-yl, 4-ethylcyclohex-1-en-1-yl, 4-t-butylcyclohex-1-en-1-yl, cyclopentyl, 1-methylcyclopentyl, 1-methylcyclopentoxy, 5,5-dimethylcyclopent-1-en-1-yl, 4-methylcyclopent-1-en-1-yl, cycloheptyl or cyclohept-1-en-1-yl or where $R^3$ is chlorodifluoromethyl if R is cyclopentyl or cycloheptyl or where $R^3$ is trifluoromethyl if R is cyclohexyl, 3-methylcyclohexyl, 4-t-butylcyclohexyl, cyclohexyloxy, 4-methylcyclohexyloxy, 2,6-dimethylcyclohexyloxy, cyclohex-1-en-1-yl, 4-ethylcyclohex-1-en-1-yl, 2-isopropylcyclohex-1-en-1-yl, 6-isopropylcyclohex-1-en-1-yl, 4-t-butylcyclohex-1-en-1-yl, 6-ethyl-2-methylcyclohex-1-en-1-yl, 6-isopropylcyclohex-1-en-1-yl, cyclopentyl, 1-methylcyclopentyl, 1-methylcyclopentoxy, 2-methylcyclopent-1-en-1-yl, 3-methylcyclopent-1-en-1-yl, 4-methylcyclopent-1-en-1-yl, cycloheptyl or cyclohept-1-en-1-yl.

The invention additionally relates to the preparation of these compounds, compositions containing them and their use for controlling harmful fungi, in particular Botrytis.

N-(2-Methylphenyl)-3-methylthiophene-2-carboxamide, N-(2-methylphenyl)-2,5-dimethylthiophene-3-carboxamide and N-(2-methylphenyl)-1,3,5-trimethylpyrazole-4-carboxamide are known from the literature as fungicidal active compounds (DE-A 2 701 091; Pestic. Biochem. Physiol., 25 (2), (1986) 188–204).

The subsequently published application WO-A 93/11,117 additionally describes the pyrazolecarboxanilides excluded from the compounds I as being fungicidally active.

It is an object of the present invention to provide novel fungicidally active compounds having an improved spectrum of action.

We have found that this object is achieved by the compounds I defined at the beginning.

We have additionally found processes for preparing these compounds, compositions containing them and their use for controlling harmful fungi.

The compounds I are in general obtained by reacting a carboxylic acid halide of the formula II in a manner known per se (e.g. J. March, Advanced Organic Chemistry, 2nd Ed., 1977, 382 ff., McGraw-Hill) with an aniline of the formula III in the presence of a base.

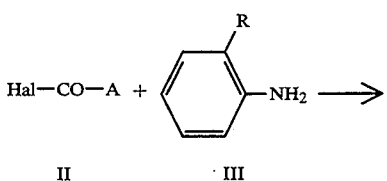

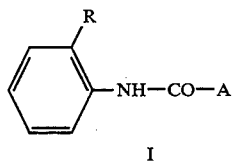

The radical Hal in the formula II is a halogen such as chlorine, bromine or iodine, in particular chlorine or bromine. This reaction is customarily carried out at temperatures from −20° C. to 100° C., preferably 0° C. to 50° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide and dimethylformamide, particularly preferably toluene and tetrahydrofuran.

Mixtures of the solvents mentioned can also be used.

Suitable bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate and also alkali metal hydrogencarbonates such as sodium hydrogencarbonate, and organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium, additionally organic bases, e.g. tertiary amines such as trimethylamine, triethylamine, tri-isopropylethylamine and N-methylpiperidine, pyridine, substituted pyridines such as collidine, lutidine and 4-dimethylaminopyridine and also bicyclic amines.

Triethylamine and pyridine are particularly preferably used.

The bases are in general employed in equimolar amounts based on the compound II. However, they can also be used in an excess of from 5 mol % to 30 mol %, preferably 5 mol % to 10 mol %, or—in the case of the use of tertiary amines—if appropriate as a solvent.

The starting materials are in general reacted with one another in equimolar amounts. It may be advantageous for the yield to employ II in an excess of from 1 mol % to 20 mol %, preferably 1 mol % to 10 mol %, based on III.

The starting substances of the formulae II and III needed for preparing the compounds I are known or can be synthesized analogously to the known compounds (Helv. Chim. Acta, 60, (1977) 978; Zh. Org. Khim., 26, (1990) 1527; Heterocycles 26, (1987) 1885; Izv. Akad. Nauk. SSSR Ser. Khim., (1982) 2160; THL 28 593 (1987); THL 29, (1988) 5463).

Compounds I in which A is a 2-aminothiazole A4 are obtained particularly advantageously by first preparing the corresponding N-phenyl-2-halothiazole-5-carboxanilide V from a 2-halothiazole-5-carboxylic acid halide of the formula IV and an aniline of the formula III and then reacting V with ammonia to give the corresponding carboxanilide I.4.

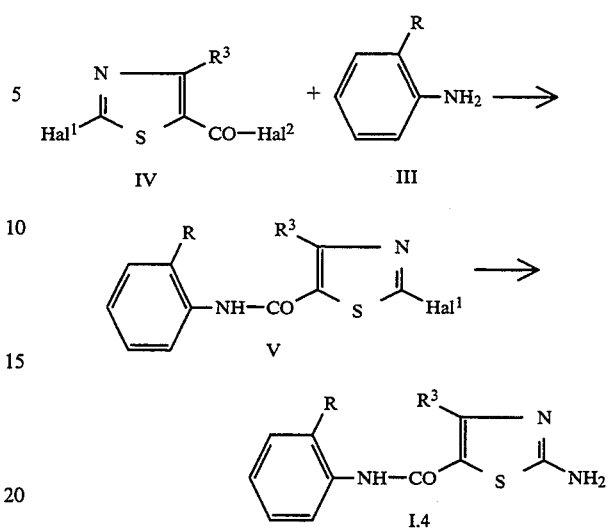

$Hal^1$ and $Hal^2$ are in each case halogens such as chlorine, bromine and iodine, chlorine being preferred in the position $Hal^1$ and chlorine and bromine being preferred in the position $Hal^2$.

The reaction of V with ammonia is carried out in a manner known per se at from 50° C. to 200° C., at from 1 to 200 atm., preferably 5 to 50 atm., in an inert solvent in the presence of a catalyst.

Suitable solvents are aliphatic hydrocarbons such as pentane, hexane, cyclohexane and petroleum ether, aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol and also dimethyl sulfoxide and dimethylformamide, particularly preferably alcohols such as ethanol and isopropanol.

Mixtures of the solvents mentioned can also be used.

Suitable catalysts are, for example, phenylsulfonic acid and hydroxybenzoic acid.

The catalyst is in general employed in amounts of from 0.1 mol % to 20 mol %, preferably from 0.5 mol % to 5 mol % based on V.

With respect to their use in fungicidal compositions, suitable compounds of the formula I are those in which the substituents have the following meanings:

R
is $C_2$–$C_{12}$-alkyl such as ethyl and straight-chain or branched propyl, butyl, pentyl, hexyl, heptyl, octyl, nonyl, decyl, undecyl and dodecyl, particularly straight-chain or branched $C_3$–$C_{10}$-alkyl such as propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl, in particular propyl, 1-methylethyl, butyl, 1-methylbutyl, 2-methylbutyl, 1,1-dimethylethyl, pentyl, 1-methylbutyl, hexyl, heptyl and 1-methylheptyl, where these groups can be partially or completely halogenated, ie. the hydrogens of these groups can be partially or completely replaced by halogens such as fluorine, chlorine and bromine, in particular fluorine and chlorine, for example haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_2$–$C_{12}$-alkoxy such as ethoxy and straight-chain or branched propoxy, butoxy, pentoxy, hexyloxy, heptyloxy, octyloxy, nonyloxy, decyloxy, undecyloxy and dodecyloxy, particularly straight-chain or branched $C_2$–$C_{10}$-alkoxy such as ethoxy, propoxy, 1-methylethoxy, butoxy, 1-methylpropoxy, 2-methylpropoxy, 1,1-dimethylethoxy, n-pentoxy, 1-methylbutoxy, 2-methylbutoxy, 3-methylbutoxy, 1,2-dimethylpropoxy, 1-ethylpropoxy, n-hexyloxy, 1-methylpentoxy, 2-methylpentoxy, 3-methylpentoxy, 4-methylpentoxy, 1,2-dimethylbutoxy, 1,3-dimethylbutoxy, 2,3-dimethylbutoxy, 1,2-dimethylbutoxy, 2,2-dimethylbutoxy, 3,3-dimethylbutoxy, 1,1,2-trimethylpropoxy, 1,2,2-trimethylpropoxy, 1-ethylbutoxy, 2-ethylbutoxy, 1-ethyl-2-methylpropoxy, n-heptyloxy, 1-methylhexyloxy, 2-methylhexyloxy, 3-methylhexyloxy, 4-methylhexyloxy, 5-methylhexyloxy, 1-ethylpentoxy, 2-ethylpentoxy, 1-propylbutoxy, octyloxy, 1-methylheptyloxy, 2-methylheptyloxy, 1-ethylhexyloxy, 2-ethylhexyloxy, 1-propylpentoxy, 2-propylpentoxy, nonyloxy, 1-methyloctyloxy, 2-methyloctyloxy, 1-ethylheptyloxy, 2-ethylheptyloxy, 1-propylhexyloxy, 2-propylhexyloxy, decyloxy, 1-methylnonyloxy, 2-methylnonyloxy, 1-ethyloctyloxy, 2-ethyloctyloxy, 1-propylheptyloxy and 2-propylheptyloxy, in particular ethoxy, propoxy, 1-methylethoxy, butoxy, 1-methylpropoxy, 2-methylpropoxy, 1,1-dimethylethoxy, pentoxy, hexyloxy and 2-ethylhexyloxy, where these groups can be partially or completely halogenated, ie. the hydrogens of these groups can be partially or completely replaced by halogens such as fluorine, chlorine and bromine, in particular fluorine and chlorine, for example haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-di-chloro-2-fluoroethoxy, 2,2,2-trichloroethoxy and pentafluoroethoxy;

$C_3$–$C_{12}$-alkenyl such as straight-chain or branched propenyl, butenyl, pentenyl, hexenyl, heptenyl, octenyl, nonenyl, decenyl, undecenyl and dodecenyl, particularly straight-chain or branched $C_3$–$C_{10}$-alkenyl such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-2-propenyl, 1-methyl-2-pentenyl, 2-methyl-2-pentenyl, 1-methyl-3-pentenyl, 2-methyl-3-pentenyl, 1-methyl-2-hexenyl, 2-methyl-2-hexenyl, 1-methyl-3-hexenyl, 2-methyl-3-hexenyl, 1-ethyl-2-pentenyl, 2-ethyl-2-pentenyl, 1-ethyl-3-pentenyl, 2-ethyl-3-pentenyl, 1-methyl-2-heptenyl, 2-methyl-2-heptenyl, 1-methyl-3-heptenyl, 2-methyl-3-heptenyl, 1-ethyl-2-hexenyl, 2-ethyl-2-hexenyl, 1-ethyl-3-hexenyl, 2-ethyl-3-hexenyl, 1-methyl-2-octenyl, 2-methyl-2-octenyl, 1-methyl-3-octenyl, 2-methyl-3-octenyl, 1-ethyl-2-heptenyl, 2-ethyl-2-heptenyl, 1-ethyl-3-heptenyl, 2-ethyl-3-heptenyl, 1-ethyl-2-octenyl, 2-ethyl-2-octenyl, 1-ethyl-3-octenyl and 2-ethyl-3-octenyl, in particular 1-propenyl, 2-propenyl, 1-methylethenyl, 1-methyl-2-propenyl, 2-methyl-2-propenyl, 1-ethyl-2-propenyl, 1-methyl-2-butenyl, 1-ethyl-2-butenyl, 1-(1-methylethyl)-2-butenyl, 1-butyl-2-butenyl, 1-methyl-2-pentenyl and 1,4-dimethyl-2-pentenyl, where these groups can be partially or completely halogenated, ie. the hydrogens of these groups can be partially or completely replaced by halogens such as fluorine, chlorine and bromine, in particular fluorine and chlorine, in particular 3-chloro-2-propenyl, 2,3-dichloro-2-propenyl, 2,3,3-trichloro-2-propenyl;

$C_3$–$C_{12}$-alkenyloxy such as straight-chain or branched propenyloxy, butenyloxy, pentenyloxy, hexenyloxy, heptenyloxy, octenyloxy, nonenyloxy, decenyloxy, undecenyloxy and dodecenyloxy, particularly straight-chain or branched $C_3$–$C_{10}$-alkenyloxy such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-2-propenyloxy, 1-methyl-2-pentenyloxy, 2-methyl-2-pentenyloxy, 1-methyl-3-pentenyloxy, 2-methyl-3-pentenyloxy, 1-methyl-2-hexenyloxy, 2-methyl-2-hexenyloxy, 1-methyl-3-hexenyloxy, 2-methyl-3-hexenyloxy, 1-ethyl-2-pentenyloxy, 2-ethyl-2-pentenyloxy, 1-ethyl-3-pentenyloxy, 2-ethyl-3-pentenyloxy, 1-methyl-2-heptenyloxy, 2-methyl-2-heptenyloxy, 1-methyl-3-heptenyloxy, 2-methyl-3-heptenyloxy, 1-ethyl-2-hexenyloxy, 2-ethyl-2-hexenyloxy, 1-ethyl-3-hexenyloxy, 2-ethyl-3-hexenyloxy, 1-methyl-2-octenyloxy, 2-methyl-2-octenyloxy, 1-methyl-3-octenyloxy, 2-methyl-3-octenyloxy, 1-ethyl-2-heptenyloxy, 2-ethyl-2-heptenyloxy, 1-ethyl-3-heptenyloxy, 2-ethyl-3-heptenyloxy, 1-ethyl-2-octenyloxy, 2-ethyl-2-octenyloxy, 1-ethyl-3-octenyloxy and 2-ethyl-3-octenyloxy, in particular 2-propenyloxy, 1-methyl-2-propenyloxy, 2-methyl-2-propenyloxy, 2-pentenyloxy, 3-pentenyloxy, 1-methyl-2-butenyloxy and 1-methyl-2-pentenyloxy, where these groups can be partially or completely halogenated, ie. the hydrogens of these groups can be partially or completely replaced by halogens such as fluorine, chlorine and bromine, in particular fluorine and chlorine, in particular 3-chloro-2-propenyloxy, 2,3-dichloro-2-propenyloxy and 2,3,3-trichloro-2-propenyloxy;

$C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, in particular 2-propynyl, 2-butynyl and 3-butynyl, where these groups can be partially or completely halogenated, ie. the hydrogens of these groups can be partially or completely replaced by halogens such as fluorine, chlorine and bromine, in particular fluorine and chlorine, for example 3-chloro-2-propynyl, 3-chloro-2-butynyl and 4-chloro-3-butynyl;

$C_3$–$C_6$-alkynyloxy such as 2-propynyloxy, 2-butynyloxy, 3-butynyloxy, 1-methyl-2-propynyloxy, 2-pentynyloxy, 3-pentynyloxy, 3-pentynyloxy, 4-pentynyloxy, 1-methyl-3-butynyloxy, 2-methyl-3-butynyloxy, 1-methyl-2-butynyloxy, 1,1-dimethyl-2-propionyloxy, 1-ethyl-2-propynyloxy, 2-hexynyloxy, 3-hexynyloxy, 4-alkynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-3-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy and 1-ethyl-1-methyl-2-propynyloxy, preferably 2-propynyloxy, 2-butynyloxy, 1-methyl-2-propynyloxy and 1-methyl-2-butynyloxy, 2-propynyloxy, 2-butynyloxy, 3-butynyloxy and 1-methyl-2-propynyloxy, where these groups can be partially or completely halogenated, ie. the hydrogens of these groups can be partially or completely replaced by halogens such as fluorine, chlorine and bromine, in particular fluorine and chlorine, for example 3-chloro-2-propynyloxy, 3-chloro-2-butynyloxy and 4-chloro-3-butynyloxy;

$C_3$–$C_7$-cycloalkyl such as cyclopropyl, cyclobutyl, cyclopentyl, cyclohexyl and cycloheptyl, where these rings can carry one to three $C_1$–$C_4$-alkyls such as methyl, ethyl, propyl, 1-methylethyl, butyl, 1-methylpropyl, 2-methylpropyl and 1,1-dimethylethyl;

$C_4$–$C_7$-cycloalkenyl such as cyclobutenyl, cyclopentenyl, cyclohexenyl and cycloheptenyl, where these rings can carry one to three $C_1$–$C_4$-alkyls such as methyl, ethyl, propyl, 1-methylethyl, butyl, 1-methylpropyl, 2-methylpropyl and 1,1-dimethylethyl;

$C_3$–$C_7$-cycloalkoxy such as cyclopropoxy, cyclobutoxy, cyclopentoxy, cyclohexyloxy and cycloheptyloxy, where these rings can carry one to three $C_1$–$C_4$-alkyls such as methyl, ethyl, propyl, 1-methylethyl, butyl, 1-methylpropyl, 2-methylpropyl and 1,1-dimethylethyl;

or $C_4$–$C_7$-cycloalkenyloxy such as 1-cyclobutenyloxy, 2-cyclobutenyloxy, 1-cyclopentenyloxy, 2-cyclopentenyloxy, 3-cyclopentenyloxy, 1-cyclohexenyloxy, 2-cyclohexenyloxy, 3-cyclohexenyloxy, 1-cycloheptenyloxy, 2-cycloheptenyloxy, 3-cycloheptenyloxy and 4-cycloheptenyloxy, where these rings can carry one to three $C_1$–$C_4$-alkyls such as methyl, ethyl, propyl, 1-methylethyl, butyl, 1-methylpropyl, 2-methylpropyl and 1,1-dimethylethyl;

phenyl, which can carry one to five halogens such as fluorine, chlorine, bromine and iodine, in particular fluorine, chlorine and bromine, and/or one to three of the following radicals:

$C_1$–$C_4$-alkyl as mentioned above;
$C_1$–$C_4$-haloalkyl as mentioned above;
$C_1$–$C_4$-alkoxy as mentioned above;
$C_1$–$C_4$-haloalkoxy as mentioned above;
$C_1$–$C_4$-alkylthio such as methylthio, ethylthio, propylthio, 1-methylethylthio, butylthio, 1- methylpropylthio, 2-methylpropylthio and 1,1-dimethylethylthio;

or $C_1$–$C_4$-haloalkylthio, particularly $C_1$–$C_2$-haloalkylthio such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio.

A is a cyclic radical from the group consisting of the formulae A1 to A5:

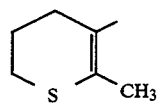

A1

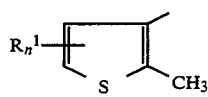

A2

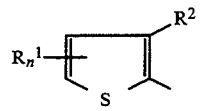

A3

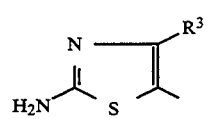

A4

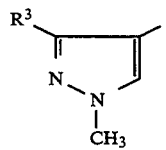

A5 where the substituents have the following meanings:
$R^1$ is hydrogen or $C_1$–$C_4$-alkyl as mentioned above;
$R^2$ is halogen as mentioned above or $C_1$–$C_4$-alkyl as mentioned above;
$R^3$ is $C_1$–$C_4$-alkyl as mentioned above or $C_1$–$C_4$-haloalkyl as mentioned above;
n is 1 or 2, where the radicals $R^1$ can be different if the value of n is 2,
where R is not phenyl if A is 3-methylthien-2-yl, excluding compounds I where A is A5 and
$R^3$ is methyl if R is cyclopentyl, cyclohexyl or cycloheptyl or where
$R^3$ is difluoromethyl if R is cyclohexyl, 4-t-butylcyclohexyl, cyclohexyloxy, cyclohex-1-en-1-yl, 2,6-dimethylcyclohex-1-en-1-yl, 4-ethylcyclohex-1-en-1-yl, 4-t-butylcyclohex-1-en-1-yl, cyclopentyl, 1-methylcyclopentyl, 1-methylcyclopentoxy, 5,5-dimethylcyclopent-1-en-1-yl, 4-methylcyclopent-1-en-1-yl, cycloheptyl or cyclohept-1-en-1-yl or where
$R^3$ is chlorodifluoromethyl if R is cyclopentyl or cycloheptyl or where
$R^3$ is trifluoromethyl if

R is cyclohexyl, 3-methylcyclohexyl, 4-t-butylcyclohexyl, cyclohexyloxy, 4-methylcyclohexyloxy, 2,6-dimethylcyclohexyloxy, cyclohex-1-en-1-yl, 4-ethylcyclohex-1-en-1-yl, 2-isopropylcyclohex-1-en-1-yl, 6-isopropylcyclohex-1-en-1-yl, 4-t-butylcyclohex-1-en-1-yl, 6-ethyl-2-methylcyclohex-1-en-1-yl, 6-isopropylcyclohex-1-en-1-yl, cyclopentyl, 1-methylcyclopentyl, 1-methylcyclopentoxy, 2-methylcyclopent-1-en-1-yl, 3-methylcyclopent-1-en-1-yl, 4-methylcyclopent-1-en-1-yl, cycloheptyl or cyclohept-1-en-1-yl.

With respect to the biological action, particularly preferred compounds of the formula I are those in which R has the abovementioned meanings and A is a cyclic radical from the group consisting of the formulae A1 to A5, in which the substituents are the following radicals:
$R^1$ is hydrogen or methyl;
$R^2$ is halogen such as fluorine, chlorine and bromine or methyl
$R^3$ is methyl or $C_1$-haloalkyl such as chloromethyl, dichloromethyl, trichloromethyl, fluoromethyl, difluoromethyl, trifluoromethyl, chlorofluoromethyl, dichlorofluoromethyl and chlorodifluoromethyl;
n is 1 or 2, where the radicals $R^1$ can be different if the value of n is 2,
where R is not phenyl if A is 3-methylthien-2-yl.

Those compounds of the formula I are particularly preferred in which R has the abovementioned meaning and A is a cyclic radical from the group consisting of the formulae A1 to A5, in which the substituents are the following groups:
$R^1$ is hydrogen or methyl;
$R^2$ is chlorine or methyl;
$R^3$ is methyl, difluoromethyl or trifluoromethyl;
n is 1 or 2, where the radicals $R^1$ can be different if the value of n is 2,
where R is not phenyl if A is 3-methylthien-2-yl.

Particularly preferred compounds of the formula I are additionally:
Compounds I in which
R is isobutyl, sec-butyl, 2-ethylbutyl, cyclopentyl, cyclohexyl, cyclopent-2-en-1-yl, phenyl or 1,1,2,2-tetrafluoroethoxy.
Compounds I in which
A is A1, A3, A4 or A5, preferably compounds I in which
A is A1, A3, A4 or A5 and
R is isobutyl, sec-butyl, 2-ethylbutyl, cyclopentyl, cyclohexyl, cyclopent-2-en-1-yl, phenyl or 1,1,2,2-tetrafluoroethoxy and
in particular compounds I in which
A is A1, A3, A4 or A5 and
R is isobutyl, sec-butyl, cyclopentyl, cyclohexyl or phenyl.
Compounds I in which
A is A1,
preferably compounds I in which
A is A1 and
R is isobutyl, sec-butyl, 2-ethylbutyl, cyclopentyl, cyclohexyl, cyclopent-2-en-1-yl, phenyl or 1,1,2,2-tetrafluoroethoxy and
in particular compounds I in which
A is A1 and R is isobutyl, sec-butyl, cyclopentyl, cyclohexyl or phenyl.

Compounds I in which
A is A3 and
R² is chlorine or methyl,
preferably compounds I in which
A is A3,
R² is chlorine or methyl and
R is isobutyl, sec-butyl, 2-ethylbutyl, cyclopentyl, cyclohexyl, cyclopent-2-en-1-yl, phenyl or 1,1,2,2-tetrafluoroethoxy,
in particular compounds I in which
A is A3,
R² is chlorine or methyl and
R is isobutyl, sec-butyl, cyclopentyl, cyclohexyl, cyclopent-2-en-1-yl or phenyl.

Compounds I in which
A is A4 and
R³ is methyl or trifluoromethyl,
preferably compounds I in which
A is A4,
R³ is methyl or trifluoromethyl and
R is isobutyl, sec-butyl, 2-ethylbutyl, cyclopentyl, cyclohexyl, cyclopent-2-en-1-yl, phenyl or 1,1,2,2-tetrafluoroethoxy and
in particular compounds I in which
A is A4,
R³ is methyl or trifluoromethyl and
R is isobutyl, sec-butyl, cyclopentyl, cyclohexyl or phenyl.

Compounds I in which
A is A5 and
R³ is methyl or trifluoromethyl,
preferably compounds I in which
A is A5,
R³ is methyl or trifluoromethyl and
R is isobutyl, sec-butyl, 2-ethylbutyl, cyclopent-2-en-1-yl, phenyl or 1,1,2,2-tetrafluoroethoxy and
in particular compounds I in which
A is A5,
R³ is methyl or trifluoromethyl and
R is isobutyl, sec-butyl, 2-ethylbutyl or 1,1,2,2-tetrafluoroethoxy.

Particularly preferred compounds of the formula I are summarized in the following Tables A to E.

TABLE A

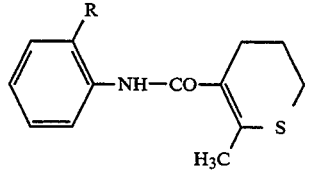

I.1

| R |
|---|
| i-$C_3H_7$ |
| n-$C_3H_7$ |
| n-$C_4H_9$ |
| sec.-$C_4H_9$ |
| i-$C_4H_9$ |
| tert.-$C_4H_9$ |
| n-$C_5H_{11}$ |
| sec-$C_5H_{11}$ |
| n-$C_6H_{13}$ |
| n-$C_7H_{15}$ |
| sec.-$C_7H_{15}$ |
| 1-Methylvinyl |
| 2-Methylvinyl |
| Allyl |
| 2-Methylallyl |

TABLE A-continued

I.1

| R |
|---|
| 2-Ethylallyl |
| 1-Methylallyl |
| 1-Ethylallyl |
| 1-Methyl-2-butenyl |
| 1-Ethyl-2-butenyl |
| 1-Isopropyl-2-butenyl |
| 1-n-Butyl-2-butenyl |
| 1-Methyl-2-pentenyl |
| 1,4-Dimethyl-2-pentenyl |
| Propargyl |
| 2-Butynyl |
| 3-Butynyl |
| Ethoxy |
| Propoxy |
| 1-Methylethoxy |
| n-Butoxy |
| 1-Methylpropoxy |
| 2-Methylpropoxy |
| 1,1-Dimethylethoxy |
| n-Pentyloxy |
| n-Hexyloxy |
| 2-Ethylhexyloxy |
| 2-Propenyloxy |
| 2-Butenyloxy |
| 2-Methyl-2-propenyloxy |
| 2-Pentenyloxy |
| 3-Pentenyloxy |
| 3-Chloro-2-propenyloxy |
| 2,3-Dichloro-2-propenyloxy |
| 2,3,3-Trichloropropenyloxy |
| 2-Propynyloxy |
| 2-Butynyl-oxy |
| 3-Butynyl-oxy |
| 1-Methyl-2-propynyloxy |
| Cyclopropyl |
| Cyclobutyl |
| Cyclopentyl |
| Cyclohexyl |
| 3-Cyclopentenyl |
| 1-Cyclopentenyl |
| 3-Cyclohexenyl |
| 1-Cyclohexenyl |
| Cyclopentyloxy |
| Cyclohexyloxy |
| 3-Cyclopentenyloxy |
| 3-Cyclohexenyloxy |
| Phenyl |
| 2-Fluorophenyl |

TABLE B

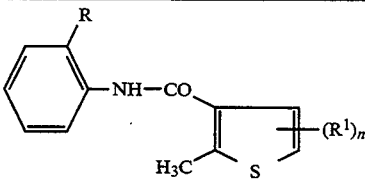

I.2

| $(R^1)_n$ | R |
|---|---|
| 5-$CH_3$ | i-$C_3H_7$ |
| 5-$CH_3$ | n-$C_3H_7$ |
| 5-$CH_3$ | n-$C_4H_9$ |
| 5-$CH_3$ | sec.-$C_4H_9$ |
| 5-$CH_3$ | i-$C_4H_9$ |
| 5-$CH_3$ | tert.-$C_4H_9$ |
| 5-$CH_3$ | n-$C_5H_{11}$ |
| 5-$CH_3$ | sec-$C_5H_{11}$ |
| 5-$CH_3$ | n-$C_6H_{13}$ |

TABLE B-continued

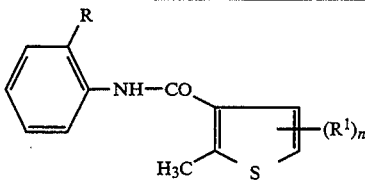

I.2

| (R¹)ₙ | R |
|---|---|
| 5-CH₃ | n-C₇H₁₅ |
| 5-CH₃ | sec.-C₇H₁₅ |
| 5-CH₃ | Ethoxy |
| 5-CH₃ | Propoxy |
| 5-CH₃ | 1-Methylethoxy |
| 5-CH₃ | n-Butoxy |
| 5-CH₃ | 1-Methylpropoxy |
| 5-CH₃ | 2-Methylpropoxy |
| 5-CH₃ | 1,1-Dimethylethoxy |
| 5-CH₃ | n-Pentyloxy |
| 5-CH₃ | n-Hexyloxy |
| 5-CH₃ | Cyclopentyl |
| 5-CH₃ | Cyclohexyl |
| 5-CH₃ | 3-Cyclopentenyl |
| 5-CH₃ | 1-Cyclopentenyl |
| 5-CH₃ | 3-Cyclohexenyl |
| 5-CH₃ | 1-Cyclohexenyl |
| 5-CH₃ | Cyclopentyloxy |
| 5-CH₃ | Cyclohexyloxy |
| 5-CH₃ | 2-Cyclopentenyloxy |
| 4,5-(CH₃)₂ | i-C₃H₇ |
| 4,5-(CH₃)₂ | n-C₃H₇ |
| 4,5-(CH₃)₂ | n-C₄H₉ |
| 4,5-(CH₃)₂ | sec.-C₄H₉ |
| 4,5-(CH₃)₂ | i-C₄H₉ |
| 4,5-(CH₃)₂ | tert.-C₄H₉ |
| 4,5-(CH₃)₂ | n-C₅H₁₁ |
| 4,5-(CH₃)₂ | sec-C₅H₁₁ |
| 4,5-(CH₃)₂ | n-C₆H₁₃ |
| 4,5-(CH₃)₂ | n-C₇H₁₅ |
| 4,5-(CH₃)₂ | sec.-C₇H₁₅ |
| 4,5-(CH₃)₂ | Ethoxy |
| 4,5-(CH₃)₂ | Propoxy |
| 4,5-(CH₃)₂ | 1-Methylethoxy |
| 4,5-(CH₃)₂ | n-Butoxy |
| 4,5-(CH₃)₂ | 1-Methylpropoxy |
| 4,5-(CH₃)₂ | 2-Methylpropoxy |
| 4,5-(CH₃)₂ | 1,1-Dimethylethoxy |
| 4,5-(CH₃)₂ | n-Pentyloxy |
| 4,5-(CH₃)₂ | n-Hexyloxy |
| 4,5-(CH₃)₂ | Cyclopentyl |

TABLE C

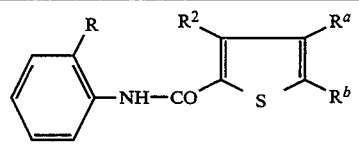

I.3

| Rᵃ | Rᵇ | R² | R |
|---|---|---|---|
| H | H | Cl | i-C₃H₇ |
| H | H | Cl | n-C₃H₇ |
| H | H | Cl | n-C₄H₉ |
| H | H | Cl | sec.-C₄H₉ |
| H | H | Cl | i-C₄H₉ |
| H | H | Cl | tert.-C₄H₉ |
| H | H | Cl | n-C₅H₁₁ |
| H | H | Cl | sec-C₅H₁₁ |
| H | H | Cl | n-C₆H₁₃ |
| H | H | Cl | n-C₇H₁₅ |
| H | H | Cl | sec.-C₇H₁₅ |
| H | H | Cl | Ethoxy |
| H | H | Cl | Propoxy |
| H | H | Cl | 1-Methylethoxy |
| H | H | Cl | n-Butoxy |
| H | H | Cl | 1-Methylpropoxy |
| H | H | Cl | 2-Methylpropoxy |

TABLE C-continued

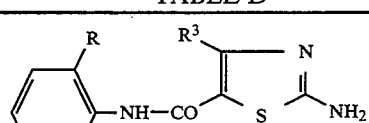

I.3

| Rᵃ | Rᵇ | R² | R |
|---|---|---|---|
| H | H | Cl | 1,1-Dimethylethoxy |
| H | H | Cl | n-Pentyloxy |
| H | H | Cl | n-Hexyloxy |
| H | H | Cl | Cyclopentyl |
| H | H | Cl | Cyclopentenyl |
| H | H | Cl | Cyclohexyl |
| H | H | Cl | Phenyl |
| H | H | CH₃ | i-C₃H₇ |
| H | H | CH₃ | n-C₃H₇ |
| H | H | CH₃ | n-C₄H₉ |
| H | H | CH₃ | sec.-C₄H₉ |
| H | H | CH₃ | i-C₄H₉ |
| H | H | CH₃ | tert.-C₄H₉ |
| H | H | CH₃ | n-C₅H₁₁ |
| H | H | CH₃ | sec-C₅H₁₁ |
| H | H | CH₃ | n-C₆H₁₃ |
| H | H | CH₃ | n-C₇H₁₅ |
| H | H | CH₃ | sec.-C₇H₁₅ |
| H | H | CH₃ | Ethoxy |
| H | H | CH₃ | Propoxy |
| H | H | CH₃ | 1-Methylethoxy |
| H | H | CH₃ | n-Butoxy |
| H | H | CH₃ | 1-Methylpropoxy |
| H | H | CH₃ | 2-Methylpropoxy |
| H | H | CH₃ | 1,1-Dimethylethoxy |
| H | H | CH₃ | n-Pentyloxy |
| H | H | CH₃ | n-Hexyloxy |
| H | H | CH₃ | Cyclopentyl |
| H | H | CH₃ | Cyclopentenyl |
| H | H | CH₃ | Cyclohexyl |
| H | H | CH₃ | Phenyl |
| CH₃ | H | CH₃ | i-C₃H₇ |
| CH₃ | H | CH₃ | n-C₃H₇ |
| CH₃ | H | CH₃ | n-C₄H₉ |
| CH₃ | H | CH₃ | sec.-C₄H₉ |
| CH₃ | H | CH₃ | i-C₄H₉ |
| CH₃ | H | CH₃ | tert.-C₄H₉ |
| CH₃ | H | CH₃ | n-C₅H₁₁ |
| CH₃ | H | CH₃ | sec-C₅H₁₁ |
| CH₃ | H | CH₃ | n-C₆H₁₃ |
| CH₃ | H | CH₃ | n-C₇H₁₅ |
| CH₃ | H | CH₃ | sec.-C₇H₁₅ |
| CH₃ | H | CH₃ | Ethoxy |
| CH₃ | H | CH₃ | Propoxy |
| CH₃ | H | CH₃ | 1-Methylethoxy |
| CH₃ | H | CH₃ | n-Butoxy |
| CH₃ | H | CH₃ | 1-Methylpropoxy |
| CH₃ | H | CH₃ | 2-Methylpropoxy |
| CH₃ | H | CH₃ | 1,1-Dimethylethoxy |
| CH₃ | H | CH₃ | n-Pentyloxy |
| CH₃ | H | CH₃ | n-Hexyloxy |
| CH₃ | H | CH₃ | Cyclopentyl |
| CH₃ | H | CH₃ | Cyclopentenyl |
| CH₃ | H | CH₃ | Cyclohexyl |
| CH₃ | H | CH₃ | Phenyl |

TABLE D

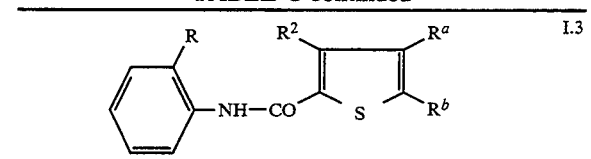

I.4

| R³ | R |
|---|---|
| CF₃ | i-C₃H₇ |
| CF₃ | n-C₃H₇ |
| CF₃ | n-C₄H₉ |
| CF₃ | sec.-C₄H₉ |
| CF₃ | i-C₄H₉ |

TABLE D-continued structure I.4: 2-R-phenyl-NH-CO-C(R³)=C(thiazole-2-amine)

| R³ | R |
|---|---|
| CF₃ | tert.-C₄H₉ |
| CF₃ | n-C₅H₁₁ |
| CF₃ | sec.-C₅H₁₁ |
| CF₃ | n-C₆H₁₃ |
| CF₃ | n-C₇H₁₅ |
| CF₃ | sec.-C₇H₁₅ |
| CF₃ | 1-Methylvinyl |
| CF₃ | 2-Methylvinyl |
| CF₃ | Allyl |
| CF₃ | 2-Methylallyl |
| CF₃ | 2-Ethylallyl |
| CF₃ | 1-Methylallyl |
| CF₃ | 1-Ethylallyl |
| CF₃ | 1-Methyl-2-butenyl |
| CF₃ | 1-Ethyl-2-butenyl |
| CF₃ | 1-Isopropyl-2-butenyl |
| CF₃ | 1-n-Butyl-2-butenyl |
| CF₃ | 1-Methyl-2-pentenyl |
| CF₃ | 1,4-Dimethyl-2-pentenyl |
| CF₃ | Propargyl |
| CF₃ | 2-Butynyl |
| CF₃ | 3-Butynyl |
| CF₃ | Ethoxy |
| CF₃ | Propoxy |
| CF₃ | 1-Methylethoxy |
| CF₃ | n-Butoxy |
| CF₃ | 1-Methylpropoxy |
| CF₃ | 2-Methylpropoxy |
| CF₃ | 1,1-Dimethylethoxy |
| CF₃ | n-Pentyloxy |
| CF₃ | n-Hexyloxy |
| CF₃ | 2-Ethylhexyloxy |
| CF₃ | 2-Propenyloxy |
| CF₃ | 2-Butenyloxy |
| CF₃ | 2-Methyl-2-propenyloxy |
| CF₃ | 2-Pentenyloxy |
| CF₃ | 3-Pentenyloxy |
| CF₃ | 3-Chloro-2-propenyloxy |
| CF₃ | 2,3-Dichloro-2-propenyloxy |
| CF₃ | 2,3,3-Trichloropropenyloxy |
| CF₃ | 2-Propynyloxy |
| CF₃ | 2-Butynyl-oxy |
| CF₃ | 3-Butynyl-oxy |
| CF₃ | 1-Methyl-2-propynyloxy |
| CF₃ | Cyclopropyl |
| CF₃ | Cyclobutyl |
| CF₃ | Cyclopentyl |
| CF₃ | Cyclohexyl |
| CF₃ | 3-Cyclopentenyl |
| CF₃ | 1-Cyclopentenyl |
| CF₃ | 3-Cyclohexenyl |
| CF₃ | 1-Cyclohexenyl |
| CF₃ | Cyclopentyloxy |
| CF₃ | Cyclohexyloxy |
| CF₃ | 3-Cyclopentenyloxy |
| CF₃ | 3-Cyclohexenyloxy |
| CH₃ | i-C₃H₇ |
| CH₃ | n-C₃H₇ |
| CH₃ | n-C₄H₉ |
| CH₃ | sec.-C₄H₉ |
| CH₃ | i-C₄H₉ |
| CH₃ | tert.-C₄H₉ |
| CH₃ | n-C₅H₁₁ |
| CH₃ | sec.-C₅H₁₁ |
| CH₃ | n-C₆H₁₃ |
| CH₃ | n-C₇H₁₅ |
| CH₃ | sec.-C₇H₁₅ |
| CH₃ | Ethoxy |
| CH₃ | Propoxy |
| CH₃ | 1-Methylethoxy |
| CH₃ | n-Butoxy |
| CH₃ | 1-Methylpropoxy |
| CH₃ | 2-Methylpropoxy |
| CH₃ | 1,1-Dimethylethoxy |
| CH₃ | n-Pentyloxy |
| CH₃ | n-Hexyloxy |
| CH₃ | Cyclopentyl |
| CH₃ | Cyclopentenyl |
| CH₃ | Cyclohexyl |
| CH₃ | 1-Ethylpropoxy |
| CH₃ | Cyclopentyloxy |
| CH₃ | 3-Cyclohexenyloxy |
| CH₃ | 2-Methyl-2-propenyloxy |
| CHF₂ | Phenyl |
| CHF₂ | 2-Fluorophenyl |

TABLE E structure I.5: 2-R-phenyl-NH-CO-C(R³)=CH-N(CH₃)-N

| R³ | R |
|---|---|
| CF₃ | i-C₃H₇ |
| CF₃ | n-C₃H₇ |
| CF₃ | n-C₄H₉ |
| CF₃ | sec.-C₄H₉ |
| CF₃ | i-C₄H₉ |
| CF₃ | tert.-C₄H₉ |
| CF₃ | n-C₅H₁₁ |
| CF₃ | sec.-C₅H₁₁ |
| CF₃ | n-C₆H₁₃ |
| CF₃ | n-C₇H₁₅ |
| CF₃ | sec.-C₇H₁₅ |
| CF₃ | 1-Methylvinyl |
| CF₃ | 2-Methylvinyl |
| CF₃ | Allyl |
| CF₃ | 2-Methylallyl |
| CF₃ | 2-Ethylallyl |
| CF₃ | 1-Methylallyl |
| CF₃ | 1-Ethylallyl |
| CF₃ | 1-Methyl-2-butenyl |
| CF₃ | 1-Ethyl-2-butenyl |
| CF₃ | 1-Isopropyl-2-butenyl |
| CF₃ | 1-n-Butyl-2-butenyl |
| CF₃ | 1-Methyl-2-pentenyl |
| CF₃ | 1,4-Dimethyl-2-pentenyl |
| CF₃ | Propargyl |
| CF₃ | 2-Butynyl |
| CF₃ | 3-Butynyl |
| CF₃ | Ethoxy |
| CF₃ | Propoxy |
| CF₃ | 1-Methylethoxy |
| CF₃ | n-Butoxy |
| CF₃ | 1-Methylpropoxy |
| CF₃ | 2-Methylpropoxy |
| CF₃ | 1,1-Dimethylethoxy |
| CF₃ | n-Pentyloxy |
| CF₃ | n-Hexyloxy |
| CF₃ | 2-Ethylhexyloxy |
| CF₃ | 2-Propenyloxy |
| CF₃ | 2-Butenyloxy |
| CF₃ | 2-Methyl-2-propenyloxy |
| CF₃ | 2-Pentenyloxy |
| CF₃ | 3-Pentenyloxy |
| CF₃ | 3-Chloro-2-propenyloxy |
| CF₃ | 2,3-Dichloro-2-propenyloxy |
| CF₃ | 2,3,3-Trichloropropenyloxy |
| CF₃ | 2-Propynyloxy |
| CF₃ | 2-Butynyl-oxy |
| CF₃ | 3-Butynyl-oxy |

TABLE E-continued

I.5

$$\text{Ar-NH-CO-C(R}^3\text{)=CH-N(CH}_3\text{)} \text{ (structure with phenyl-R, amide, enamine N-CH}_3\text{)}$$

| R³ | R |
| --- | --- |
| CF₃ | 1-Methyl-2-propynyloxy |
| CF₃ | Cyclopropyl |
| CF₃ | Cyclobutyl |
| CF₃ | 3-Cyclopentenyl |
| CF₃ | 1-Cyclopentenyl |
| CF₃ | 3-Cyclohexenyl |
| CF₃ | Cyclopentyloxy |
| CF₃ | 3-Cyclopentenyloxy |
| CF₃ | 3-Cyclohexenyloxy |
| CH₃ | i-C₃H₇ |
| CH₃ | n-C₃H₇ |
| CH₃ | n-C₄H₉ |
| CH₃ | sec.-C₄H₉ |
| CH₃ | i-C₄H₉ |
| CH₃ | tert.-C₄H₉ |
| CH₃ | n-C₅H₁₁ |
| CH₃ | sec.-C₅H₁₁ |
| CH₃ | n-C₆H₁₃ |
| CH₃ | n-C₇H₁₅ |
| CH₃ | sec.-C₇H₁₅ |
| CH₃ | Ethoxy |
| CH₃ | Propoxy |
| CH₃ | 1-Methylethoxy |
| CH₃ | n-Butoxy |
| CH₃ | 1-Methylpropoxy |
| CH₃ | 2-Methylpropoxy |
| CH₃ | 1,1-Dimethylethoxy |
| CH₃ | n-Pentyloxy |
| CH₃ | n-Hexyloxy |
| CH₃ | Cyclopentenyl |
| CH₃ | 1-Ethyl-propoxy |
| CH₃ | Cyclopentyloxy |
| CH₃ | 2-Cyclohexenyloxy |
| CH₃ | 2-Methyl-2-propenyloxy |
| CHF₂ | i-C₃H₇ |
| CHF₂ | n-C₃H₇ |
| CHF₂ | n-C₄H₉ |
| CHF₂ | sec.-C₄H₉ |
| CHF₂ | i-C₄H₉ |
| CHF₂ | tert.-C₄H₉ |
| CHF₂ | n-C₅H₁₁ |
| CHF₂ | sec.-C₅H₁₁ |
| CHF₂ | n-C₆H₁₃ |
| CHF₂ | n-C₇H₁₅ |
| CHF₂ | sec.-C₇H₁₅ |
| CHF₂ | Ethoxy |
| CHF₂ | Propoxy |
| CHF₂ | 1-Methylethoxy |
| CHF₂ | n-Butoxy |
| CHF₂ | 1-Methylpropoxy |
| CHF₂ | 2-Methylpropoxy |
| CHF₂ | 1,1-Dimethylethoxy |
| CHF₂ | n-Pentyloxy |
| CHF₂ | n-Hexyloxy |
| CHF₂ | Cyclopentenyl |
| CHF₂ | Cyclohexyl |
| CHF₂ | 1-Ethyl-propoxy |
| CHF₂ | Cyclopentyloxy |
| CHF₂ | 2-Cyclohexenyloxy |
| CHF₂ | 2-Methyl-2-propenyloxy |
| CHF₂ | Phenyl |
| CF₃ | 2-Fluorophenyl |
| CH₃ | Phenyl |
| CH₃ | 2-Fluorophenyl |
| CHF₂ | Phenyl |
| CHF₂ | 2-Fluorophenyl |

The novel active ingredients are particularly suitable for protecting various materials against degradation or destruction by bacteria or fungi or from being attacked by and covered with microorganisms. Examples of materials which can be preserved or microbicidally finished with the novel active ingredients are glues and adhesives, starch solutions, wax emulsions, clay emulsions, sizes, finishes, spinning baths, gelatine formulations, putty, joint sealants, cooling lubricants, drilling oils, fuels, plastic dispersions, emulsion paints, textiles, leather, raw hides and cosmetics. The compounds are also suitable as anti-slime agents in the paper industry, in cooling towers and in air moistening units.

The compounds I are also suitable for protecting the following plant species against attack by microorganisms:

cereals (e.g., wheat, barley, rye, oats, rice, sorghum and related species); beets (e.g., sugar and fodder beets); pomes, drupes and aggregate fruit (e.g., apples, pears, plums, peaches, almonds, cherries, strawberries, raspberries and blackberries); legumes (e.g., beans, lentils, peas, soybeans); oil-yielding crops (e.g., rape, mustard, poppies, olives, sunflowers, coconuts, castor-oil beans, cocoa beans, groundnuts); cucurbits (e.g., pumpkins, cucumbers, melons); fiber-yielding plants (e.g., cotton, flax, hemp, jute); citrus fruit (e.g., oranges, lemons, grapefruit, tangerines); vegetables (e.g., spinach, lettuce, asparagus, cabbage varieties, carrots, onions, tomatoes, potatoes, paprika); laurel species (e.g., avocado, cinnamomum, camphor) or plants such as Indian corn, tobacco, nuts, coffee, sugar cane, tea, grapes, hops, and banana and rubber trees. For the purposes of the present invention, the term "plants" is also taken to mean all types of other green growth, whether ornamentals, grassy areas, embankments, or generally low-growing cover crops.

For example the following microorganisms may be combatted with the novel compounds I:

*Straphylococcus aureus, Escherichia coli, Klebsielle pneumoniae, Citrobacter freundii, Proteus vulgaris, Pseudomonas aeruginosa, Desulfovibrio desulfuricans, Streptoverticillium rubrireticuli, Aspergillus niger, Aspergillus versicolor, Penicillium funiculosum, Penicillium expansum, Penicillium glaucum, Paecilomyces variotii, Trichoderma viride, Chaetomium globosum, Aspergillus amstelodami, Phoma pigmentovora, Phoma violacea, Aureobasidium pullulans, Saccharomyces cerevisiae, Alternaria tenuis, Stemphylium macrosporoideum, Cladosporium herbarum, Cladosporium resinae, Candida albicans, Trichophyton mentagrophytes, Geotrichum candidans, Monilia sitophila, Scenedesmus quadricauda, Chlorella vulgaris, Nostoc muscorium, Oscillatoria limosa* and *Anabaena constricta.*

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

The fungicides generally contain from 0.1 to 95, and preferably from 0.5 to 90, wt % of active ingredient. The active ingredients are used in a purity of from 90 to 100, and preferably from 95 to 100, % (according to the NMR/HPLC/GC spectrum).

Usual application concentrations are—based on the weight of the material to be protected—from 0.001 to 5, and preferably from 0.01 to 2, wt % of active ingredient; when the active ingredients are used for treating water, in oil production, in drilling and cutting oils, fuels, in swimming baths, cooling towers, air moistening units or in the paper industry, amounts of from 5 to 500 ppm are sufficient. Ready-to-use disinfectant solutions contain for instance from 0.5 to 10 wt % of active ingredient.

Examples of such formulations are given below:

I. A solution of 90 parts by weight of compound no. 7 and 10 parts by weight of N-methyl-α-pyrrolidone, which is suitable for application in the form of very fine drops.

II. A mixture of 20 parts by weight of compound no. 2, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in 100,000 parts by weight of water, an aqueous dispersion is obtained.

III. An aqueous dispersion of 20 parts by weight of compound no. 4, 40 parts by weight of cyclohexanone, 30 parts by weight of isobutanol, 20 parts by weight of the adduct of 40 moles of ethylene oxide and 1 mole of castor oil. A mixture of this dispersion with 100,000 parts by weight of water contains 0.02 wt % of the active ingredient.

IV. An aqueous dispersion of 20 parts by weight of compound no. 3, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. The mixture of this dispersion with 100,000 parts by weight of water contains 0.02 wt % of the active ingredient.

V. A hammer-milled mixture of 80 parts by weight of compound no. 1, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in 20,000 parts by weight of water, a spray liquor containing 0.1 wt % of the active ingredient is obtained.

VI. An intimate mixture of 3 parts by weight of compound no. 5 and 97 parts by weight of particulate kaolin. The dust contains 3 wt % of the active ingredient.

VII. An intimate mixture of 30 parts by weight of compound no. 6, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 4, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 5, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

X. A hammer-milled mixture of 10 parts by weight of compound no. 1, 4 parts by weight of the sodium salt of diisobutylnaphthalene-α-sulfonic acid, 20 parts by weight of the sodium salt of a lignin-sulfonic acid obtained from a sulfite waste liquor, 38 parts by weight of silica gel, and 38 parts by weight of kaolin. By finely dispersing the mixture in 10,000 parts by weight of water, a spray liquor containing 0.1 wt % of the active ingredient is obtained.

Used alone, the active ingredients act as low-foaming biocides. A significant increase in the action of biocidal formulations containing these compounds is achieved if tri-$C_6$- to $C_{12}$-alkylmethylammonium salts, preferably in amounts of from 20 to 40 wt %, based on the weight of compounds of the general formula I, are added.

The active ingredients may also be mixed with other, prior art, microbicides. In many instances, a synergistic effect is achieved, i.e., the microbicidal action of the mixture is greater than the added actions of its individual components.

Prior art microbicides may be added to the novel substances in a weight ratio of from 1:100 to 100:1.

Examples of such active ingredients are as follows:

2-(thiocyanomethylthio)-benzothiazole
1-[2-(2,4-dichlorophenyl)-2-(2-propenyloxy)-ethyl]-1H-imidazole
2,4,5,6-tetrachloroisophthalodinitrile
methylene bisthiocyanate
tributyltin oxide, naphthenate, benzoate, salicylate
mercaptobenzothiazole
1,2-benzisothiazolone and its alkali metal salts
alkali metal compounds of N'-hydroxy-N-cyclohexyldiazenium oxide
2-(methoxycarbonylamino)-benzimidazole
2-methyl-3-oxo-5-chlorothiazolin-3-one
trihydroxymethylnitromethane
glutardialdehyde
chloroacetamide
polyhexamethylene bisguanide
5-chloro-2-methyl-4-isothiazolin-3-one+magnesium salts
3,5-dimethyltetrahydro-1,3,5-2H-thiadiazine-2-thione
hexahydrotriazine
N,N-methylolchloroacetamide
2-n-octyl-4-isothiazolin-3-one
oxazolidines
bisoxazolidines
2,5-dihydro-2,5-dialkoxy-2,5-dialkylfurans
diethyldodecylbenzylammonium chloride
dimethyloctadecyldimethylbenzylammonium chloride
dimethyldidecylammonium chloride
dimethyldidodecylammonium chloride
trimethyltetradecylammonium chloride
benzyldimethylalkyl-($C_{12}$–$C_{18}$)-ammonium chloride
dichlorobenzyldimethyldodecylammonium chloride cetylpyridinium chloride
cetylpyridinium bromide
cetyltrimethylammonium chloride
laurylpyridinium chloride
laurylpyridinium bisulfate
benzyldodecyldi(beta-oxyethyl)-ammonium chloride
dodecylbenzyltrimethylammonium chloride
n-alkyldimethylbenzylammonium chloride
(alkyl radical: 40% $C_{12}$, 50% $C_{14}$, 10% $C_{16}$)
lauryldimethylethylammonium ethyl sulfate
n-alkyldimethyl-(1-naphthylmethyl)-ammonium chloride
(alkyl radical: 98% $C_{12}$, 2% $C_{14}$)
cetyldimethylbenzylammonium chloride
lauryldimethylbenzylammonium chloride Examples of further compounds which may be admixed are:

1,3-dimethylol-5,5-dimethylhydantoin
dimethylolurea
tetramethylolacetylenediurea
dimethylolglyoxalmonoureine
hexamethylenetetramine
glyoxal
glutardialdehyde
N-methylolchloroacetamide
1-(hydroxymethyl)-5,5-dimethylhydantoin
1,3-bis-(hydroxymethyl)-5,5-dimethylhydantoin
imidazolidinylurea
1-(3-chloroallyl)-3,5,7-triaza-1-azonia-adamantan chloride
1,3-bis-($\beta$-ethylhexyl)-5-methyl-5-amino-hexahydropyrimidine
1,3,5-tris-(hydroxyethyl)-1,3,5-hexahydrotriazine
1,2-dibromo-2,4-dicyanobutane
5-bromo-5-nitro-1,3-dioxane
2-bromo-2-nitropropanediol
1,1'-hexamethylene-bis-[5-(4-chlorophenyl)-biguanide]
4,4-diaminodiphenoxypropane
2-bromo-2-nitropropane-1,3-diol
sorbic acid and its salts
p-hydroxybenzoic acid and its esters and salts
zinc-2-pyridinethiol-N-oxide
2-[(hydroxylmethyl)amino]-ethanol
dithio-2,2'-bis(benzmethylamide)
5-chloro-2-(2,4-dichlorophenoxy)-phenol
thio-bis-(4-chlorophenol)
o-phenylphenol
chloromethyl-diiodomethylsulfone
p-chlorophenyl-3-iodopropargylformal.

SYNTHESIS EXAMPLES

The directions given in the synthesis examples below were used, after appropriate modification of the starting materials, to obtain further compounds I. The compounds thus obtained are listed in the tables below with their physical data.

1. N-(2-(1-Methylethyl)phenyl)-1-methyl-3-trifluoromethylpyrazole-4-carboxamide

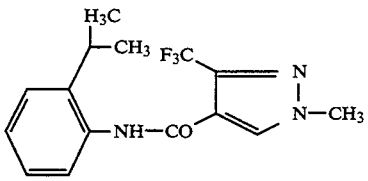

a) Ethyl 1-methyl-3-trifluoromethylpyrazole-4-carboxylate

At $-35°$ to $-40°$ C., 7.20 g of ethyl ethoxymethyl-4,4,4-trifluoroacetate is dripped into a solution of 1.38 g of methylhydrazine in 30 ml of ethanol, and the mixture is stirred for 1 hour at 0° C. and for 1 hour at 40° C. After evaporation of the solvent there is isolated 6.02 g of crystals of melting point 52°–54° C., which consisted to the extent of 85% of the above ester and 15% of ethyl 1-methyl-5-trifluoromethylpyrazole-4-carboxylate.

b) 1-Methyl-3-trifluoromethylpyrazole-4-carboxylic acid 41.5 g of the above crude product from a) is introduced into 7.4 g of sodium hydroxide in 187 ml of water, 3 ml of ethanol is added and the mixture is stirred for 12 hours at room temperature. The small amount of residue is filtered off, and the filtrate is acidified with concentrated hydrochloric acid to a pH of 3. After the product has been suction filtered, washed with cold water and dried, there is isolated 29.0 g of the above acid of m.p. 201°–202° C.

c) 1-Methyl-3-trifluoromethylpyrazol-4-carboxylic acid-2'-sec.-butylanilide

At 0° C., 1.90 g of thionyl chloride is dripped into a solution of 2.91 g of the acid from b) and 1.60 g of triethylamine in 30 ml of dichloromethane, and the mixture is stirred for 3 hours at 0° C. At the same temperature, a mixture of 2.43 g of 2-sec.-butylaniline and 1.60 g of triethylamine is then dripped in and the mixture is stirred for 12 hours at room temperature. After the batch has been washed with 60 ml of water and dried, and the solvent has been evaporated, there is isolated 4.30 g of crude product from which recrystallization with cyclohexane gives 3.50 g of the above anilide of m.p. 126°–129° C.

EXAMPLE 2

At 0° C., 2.4 g of triethylamine is added to a solution of 3.25 g of 3-chlorothiophene-2-carboxylic acid in 40 ml of dichloromethane, 2.62 g of thionyl chloride is added at 0° C., and the mixture is stirred for 16 hours at room temperature. After cooling to 0° C., a mixture of 3.28 g of 2-isobutylaniline and 2.4 g of triethylamine is dripped in and the resultant mixture is stirred for 12 hours at room temperature. After the batch has been washed with 50 ml of 8% strength sulfuric acid, 30 ml of water, 30 ml of 10% strength sodium bicarbonate solution and 30 ml of water, there is obtained 4.6 g of an oil which, after purification by column chromatography over silica gel using a 99:1 mixture of cyclohexane and ethyl acetate, gives 3.6 g of 3-chlorothiophene-2-carboxylic acid-2-isobutylaniline as an oil.

EXAMPLE 3 a) At 0° C., 2.5 g of 2-chloro-4-trifluoromethyl-5-thiazolecarboxylic chloride (J. Het. Chem. 22, 1621 (1985)) is dripped into a solution of 1.5 g of 2-isobutylaniline and 1.0 g of triethylamine in 12 ml of tetrahydrofuran. After the reaction mixture has been stirred for 12 hours at room temperature, it is diluted with 250 ml of water and extracted twice, each time with 70 ml of ethyl acetate. After drying, filtering and evaporating off the solvent, and after the crude product has been made into a paste with diisopropyl ether, there is isolated 2.8 g of 2-chloro-4-trifluoromethyl-5-thiazolecarboxylic acid-2'-isobutylanilide of m.p. 107°–108° C.

b) 30 ml of ammonia is pressured into a solution of 9.0 g of the above product and 0.7 g of phenol-4-sulfonic acid (65% strength) in 100 ml of ethanol in an autoclave, and the mixture is stirred at 120° C. for 24 hours. After the pressure has been released, the charge is filtered and evaporated down, and the crude product is partitioned between 300 ml of ethyl acetate and 100 ml of water. After drying and evaporation of the solvent, there is isolated from the organic phase 7.0 g of 2-amino-4-trifluoromethyl-5-thiazolecarboxylic acid-2'-isobutylanilide of m.p. 193–196.

TABLE 1

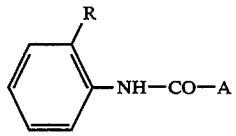

| Ex. no. | R | A | Phys. data [m.p. (°C.)] |
|---|---|---|---|
| 1 | CH(CH$_3$)CH$_2$CH$_3$ | Al | 106–107 |
| 2 | CH$_2$CH(CH$_3$)$_2$ | Al | 105–108 |
| 3 | CH(CH$_3$)CH$_2$CH$_3$ | 3-Cl-thien-2-yl | oil |
| 4 | CH$_2$CH(CH$_3$)$_2$ | 3-Cl-thien-2-yl | oil |
| 5 | CH(CH$_3$)CH$_2$CH$_3$ | 2-NH$_2$-4-CF$_3$-thiazol-5-yl | 189–195 |
| 6 | CH$_2$CH(CH$_3$)$_2$ | 2-NH$_2$-4-CF$_3$-thiazol-5-yl | 193–196 |
| 7 | CH(CH$_3$)CH$_2$CH$_3$ | 1-CH$_3$-3-CF$_3$-pyrazol-4-yl | 126–129 |
| 8 | CH(CH$_3$)CH$_2$CH$_3$ | 2-NH$_2$, 4-CH$_3$-thiazol-5-yl | 229–232 |
| 9 | CH$_2$CH(CH$_3$)$_2$ | 2-NH$_2$, 4-CH$_3$-thiazol-5-yl | 219–220 |
| 10 | Cyclopentyl | 2-NH$_2$, 4-CH$_3$-thiazol-5-yl | 256–257 |
| 11 | Cyclohexy | 2-NH$_2$, 4-CH$_3$-thiazol-5-yl | 300–301 |
| 12 | Phenyl | 2-NH$_2$, 4-CH$_3$-thiazol-5-yl | 277–278 |
| 13 | Cyclopentyl | 2-NH$_2$, 4-CF$_3$-thiazol-5-yl | 208–209 |
| 14 | Cyclohexyl | 2-NH$_2$, 4-CF$_3$-thiazol-5-yl | 242–246 |
| 15 | Phenyl | 2-NH$_2$, 4-CF$_3$-thiazol-5-yl | 214–217 |
| 16 | CH$_2$CH(CH$_3$)$_2$ | 1-CH$_3$, 3-CF$_3$-pyrazol-4-yl | 137–139 |
| 17 | CH(CH$_3$)CH$_2$CH$_3$ | 1,3-(CH$_3$)$_3$-pyrazol-4-yl | 158–160 |
| 18 | CH$_2$CH(CH$_3$)$_2$ | 1,3-(CH$_3$)$_3$-pyrazol-4-yl | 121–123 |
| 19 | OCF$_2$CHF$_2$ | 1,3-(CH$_3$)$_3$-pyrazol-4-yl | 114–115 |
| 20 | CH$_2$CH(CH$_2$CH$_3$)$_2$ | 1,3-(CH$_3$)$_3$-pyrazol-4-yl | 91–93 |
| 21 | Cyclopentyl | Al | 130–133 |
| 22 | Cyclohexyl | Al | 126–128 |
| 23 | Phenyl | Al | 93–94 |
| 24 | Cyclopentyl | 3-Cl-thien-2-yl | oil |
| 25 | Cyclopent-2-en-1-yl | 3-Cl-thien-2-yl | oil |
| 26 | Cyclohexyl | 3-Cl-thien-2-yl | oil |
| 27 | Phenyl | 3-Cl-thien-2-yl | 96–99 |
| 28 | CH(CH$_3$)CH$_2$CH$_3$ | 3-CH$_3$-thien-2-yl | oil |
| 29 | CH$_2$CH(CH$_3$)$_2$ | 3-CH$_3$-thien-2-yl | 78–80 |
| 30 | Cyclopentyl | 3-CH$_3$-thien-2-yl | oil |
| 31 | Cyclohexyl | 3-CH$_3$-thien-2-yl | 95–97 |
| 32 | Phenyl | 3-CH$_3$-thien-2-yl | oil |
| 33 | CH(CH$_3$)CH$_2$CH$_3$ | 1-CH$_3$, 3-CHF$_2$-pyrazol-4-yl | 97–100 |
| 34 | CH$_2$CH(CH$_3$)$_2$ | 1-CH$_3$, 3-CHF$_2$-pyrazol-4-yl | 122–126 |
| 35 | Phenyl | 1-CH$_3$, 3-CHF$_2$-pyrazol-4-yl | 115–118 |
| 36 | Phenyl | 1-CH$_3$, 3-CF$_3$-pyrazol-4-yl | 147–148 |
| 37 | 4-Cl-phenyl | 1-CH$_3$, 3-CF$_3$-pyrazol-4-yl | 151–153 |
| 38 | 4-OCH$_3$-phenyl | 1-CH$_3$, 3-CF$_3$-pyrazol-4-yl | 152–154 |
| 39 | 4-F-phenyl | 1-CH$_3$, 3-CF$_3$-pyrazol-4-yl | 156–157 |
| 40 | 3-Cl-phenyl | 1-CH$_3$, 3-CF$_3$-pyrazol-4-yl | 92–94 |

TABLE 1-continued

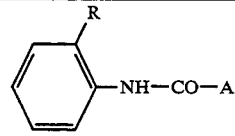

| Ex. no. | R | A | Phys. data [m.p. (°C.)] |
|---|---|---|---|
| 41 | 2-CH$_3$-phenyl | 1-CH$_3$, 3-CF$_3$-pyrazol-4-yl | 119–122 |
| 42 | CH$_2$CH(C$_2$H$_5$)$_2$ | 1-CH$_3$, 3-CF$_3$-pyrazol-4-yl | 83–85 |
| 43 | OCF$_2$CHF$_2$ | 1-CH$_3$, 3-CF$_3$-pyrazol-4-yl | 96–98 |
| 44 | Phenyl | 1,3-(CH$_3$)$_2$-pyrazol-4-yl | 158–160 |
| 45 | 4-Cl-phenyl | 1,3-(CH$_3$)$_2$-pyrazol-4-yl | 165–166 |
| 46 | 4-OCH$_3$-phenyl | 1,3-(CH$_3$)$_2$-pyrazol-4-yl | 156–157 |
| 47 | 4-F-phenyl | 1,3-(CH$_3$)$_2$-pyrazol-4-yl | 175–176 |
| 48 | 3-Cl-phenyl | 1,3-(CH$_3$)$_2$-pyrazol-4-yl | 104–106 |
| 49 | 2-CH$_3$-phenyl | 1,3-(CH$_3$)$_2$-pyrazol-4-yl | 137–139 |

Examples illustrating the biological action:

Use Example

Action on *Botrytis cinerea* in paprika

Paprika seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed for 5 days at 22° to 24° C. in a chamber of high humidity.

After this time, the untreated control plants exhibited 80% fungus attack, whereas the plants treated with 500 ppm of compounds nos. 2, 5, 7, 8, 9, 12, 13, 14, 15, 17, 18, 19 and 20 exhibited 15% attack at most.

We claim:

1. A carboxanilide of the formula I

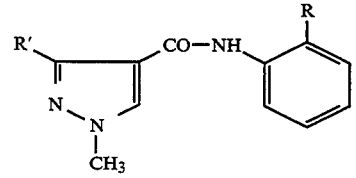

where the substituents have the following meanings:
R is C$_3$–C$_{12}$-alkyl, C$_2$–C$_{12}$-alkoxy, C$_3$–C$_{12}$-alkenyl, C$_4$–C$_{12}$-alkenyloxy, C$_4$–C$_6$-alkynyl, C$_3$–C$_6$-alkynyloxy, where these groups can be partially or completely halogenated; phenyl, which can carry one to five halogens and/or one to three of the following radicals: C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio or C$_1$–C$_4$-haloalkylthio;
R$^1$ is C$_1$–C$_4$-alkyl or C$_1$–C$_4$-haloalkyl.

2. A carboxanilide of the formula I as defined in claim 1, where R has the meanings given in claim 1 and R$^1$ is methyl or C$_1$-haloalkyl.

3. A carboxanilide of the formula I as defined in claim 1, where R has the meanings given in claim 1 and R$^1$ is methyl, difluoromethyl or trifluoromethyl.

4. An agent for combatting harmful fungi and containing a fungicidal amount of a compound of the formula I as defined in claim 1, and inert additives.

5. A process for combatting harmful fungi, wherein the fungi, their habitat and/or the plants or materials to be kept free from the fungi are treated with a fungicidally effective amount of a compound of the formula I as defined in claim 1.

6. The process of claim 5, wherein the fungus combatted is Botrytis.

* * * * *

UNITED STATES PATENT AND TRADEMARK OFFICE
CERTIFICATE OF CORRECTION

PATENT NO. : 5,438,070

DATED : August 1, 1995

INVENTOR(S) : EICKEN et al.

It is certified that error appears in the above-indentified patent and that said Letters Patent is hereby corrected as shown below:

Column 24, claim 1, line 45, "$C_3$-$C_{12}$-" should be -- $C_4$-$C_{12}$- --, both occurrences.

Column 24, claim 1, line 46, "$C_3$-$C_6$-" should be -- $C_4$-$C_6$- --.

Column 24, claim 6, line 67, "Botrytis" should be --*Botrytis*--.

Signed and Sealed this

Third Day of October, 1995

Attest:

BRUCE LEHMAN

Attesting Officer    Commissioner of Patents and Trademarks